(12) United States Patent
Ohki

(10) Patent No.: US 10,980,558 B2
(45) Date of Patent: Apr. 20, 2021

(54) ENDOSCOPE AND TREATMENT TOOL-STANDING MECHANISM

(71) Applicant: FUJIFILM Corporation, Tokyo (JP)

(72) Inventor: Tomohiro Ohki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 412 days.

(21) Appl. No.: 15/908,811

(22) Filed: Mar. 1, 2018

(65) Prior Publication Data

US 2018/0185045 A1   Jul. 5, 2018

Related U.S. Application Data

(63) Continuation of application No. PCT/JP2016/074021, filed on Aug. 17, 2016.

(30) Foreign Application Priority Data

Sep. 2, 2015 (JP) .............................. JP2015-172801

(51) Int. Cl.
*A61B 17/29* (2006.01)
*G02B 23/24* (2006.01)
(Continued)

(52) U.S. Cl.
CPC .............. *A61B 17/29* (2013.01); *A61B 1/005* (2013.01); *A61B 1/00098* (2013.01);
(Continued)

(58) Field of Classification Search
CPC .......................... A61B 1/00098; A61B 1/00101
(Continued)

(56) References Cited

U.S. PATENT DOCUMENTS 5,562,600 A   10/1996   Matsuno
5,707,344 A    1/1998   Nakazawa et al.
(Continued)

FOREIGN PATENT DOCUMENTS

CN   201082155   7/2008
CN   103908305   7/2014
(Continued)

OTHER PUBLICATIONS

"Office Action of China Counterpart Application," dated Mar. 4, 2019, with English translation thereof, p. 1-p. 19.
(Continued)

*Primary Examiner* — Alexandra L Newton
(74) *Attorney, Agent, or Firm* — JCIPRNET

(57) ABSTRACT

There is provided an endoscope and a treatment tool-standing mechanism that allows a distal-end-portion body to be reduced in size while ensuring good operability of a standing base. In a distal-end-portion body of an endoscope, a standing lever is connected to a standing base through a rotating shaft, and the standing base is rotated by the rotation of the standing lever about the rotating shaft that is caused by the push and pull of an operation wire. The standing lever includes a first arm portion that extends from the rotating shaft and a second arm portion that extends in a direction different from the direction of the first arm portion, and a useless space formed on the proximal end side of the distal-end-portion body is reduced depending on the shape of the standing lever.

4 Claims, 15 Drawing Sheets

(51) Int. Cl.
*A61B 1/00* (2006.01)
*A61B 1/005* (2006.01)
*A61B 1/06* (2006.01)

(52) U.S. Cl.
CPC ........ *A61B 1/00114* (2013.01); *A61B 1/0661* (2013.01); *G02B 23/24* (2013.01); *A61B 2017/2902* (2013.01); *A61B 2017/2903* (2013.01)

(58) Field of Classification Search
USPC ........................................................ 600/107
See application file for complete search history.

(56) References Cited

U.S. PATENT DOCUMENTS

| 2001/0044570 | A1 | 11/2001 | Ouchi et al. |
| 2010/0228086 | A1 | 9/2010 | Ohki et al. |
| 2015/0173711 | A1* | 6/2015 | Hiraoka ............... A61B 8/4494 600/466 |
| 2016/0367114 | A1* | 12/2016 | Iizuka .................... A61B 1/05 |
| 2018/0153377 | A1* | 6/2018 | Kodama ............ A61B 1/00101 |

FOREIGN PATENT DOCUMENTS

| JP | H0856900 | 3/1996 |
| JP | 2002017663 | 1/2002 |
| JP | 2003305002 | 10/2003 |
| JP | 2005304586 | 11/2005 |
| JP | 2010253234 | 11/2010 |
| JP | 2014132923 | 7/2014 |

OTHER PUBLICATIONS

"Search Report of Europe Counterpart Application", dated Jul. 3, 2018, p. 1-p. 6.

"Notification of Reasons for Refusal of Japan Counterpart Application," dated Nov. 9, 2018, with English translation thereof, p. 1-p. 4.

"International Search Report (Form PCT/ISA/210) of PCT/JP2016/074021," dated Oct. 11, 2016, with English translation thereof, pp. 1-4.

"Written Opinion of the International Searching Authority (Form PCT/ISA/237) of PCT/JP2016/074021," dated Oct. 11, 2016, with English translation thereof, pp. 1-7.

* cited by examiner

ENDOSCOPE AND TREATMENT TOOL-STANDING MECHANISM

CROSS-REFERENCE TO RELATED APPLICATIONS

This application is a Continuation of PCT International Application No. PCT/JP2016/074021 filed on Aug. 17, 2016, which claims priority under 35 U.S.C. § 119(a) to Japanese Patent Application No. 2015-172801 filed on Sep. 2, 2015. Each of the above applications is hereby expressly incorporated by reference, in their entirety, into the present application.

BACKGROUND OF THE INVENTION

1. Field of the Invention

The present invention relates to an endoscope and a treatment tool-standing mechanism (forceps elevating mechanism), and more particularly, to an endoscope and a treatment tool-standing mechanism including a treatment tool-standing base (forceps elevator) (hereinafter, referred to as a standing base).

2. Description of the Related Art

In a case in which a treatment tool is inserted into in an endoscope, into which various treatment tools can be inserted, from a treatment tool insertion opening provided in an operation unit of the endoscope, the treatment tool is inserted into an insertion part of the endoscope and is led out of a treatment tool outlet that is opened to a distal-end-portion body of the insertion part. For example, a forceps, a snare, a guide wire, an imaging tube, a puncture needle, and the like are used as treatment tools.

Since the lead-out direction of such a treatment tool needs to be changed in a distal-end-portion body of the endoscope so that treatment is performed at a desired position on a subject, a standing base for changing the lead-out direction of the treatment tool and a drive mechanism for the standing base are provided in the distal-end-portion body of the endoscope as a treatment tool-standing mechanism.

A mechanism, which allows a standing base to stand and fall by an operation member of an operation unit by a standing lever and an operation wire connected to the standing base, is disclosed in each of JP2010-253234A and JP2002-17663A as a treatment tool-standing mechanism in the related art.

According to the treatment tool-standing mechanism disclosed in JP2010-253234A, a standing base (treatment tool-standing base), which is disposed in a standing base-receiving slit (treatment tool-standing space) of a distal-end-portion body of the endoscope, and a standing lever (driven lever), which is received in a standing lever-receiving chamber (lever-receiving space) formed in the standing base-receiving slit by a partition wall (side wall portion), are connected to each other by a rotating shaft member (rotational movement shaft) that is inserted into the partition wall and is pivotally supported along a direction substantially perpendicular to the longitudinal axis of the insertion part. The standing lever extends in a direction substantially perpendicular to the rotating shaft member, and an operation wire is connected to the distal end portion of the standing lever.

Accordingly, in a case in which the operation wire is operated so as to be pushed and pulled by the operation member of the operation unit of the endoscope, the standing lever is rotated about a rotating shaft. Further, since the rotating shaft member and the standing base are also rotated about the rotating shaft while interlocking with the rotation of the standing lever, the standing base is operated to fall between a standing position and a falling position.

Furthermore, JP2002-17663A also discloses a treatment tool-standing mechanism that is the same as the treatment tool-standing mechanism disclosed in JP2010-253234A and allows the standing base to stand and fall by rotating a standing lever (standing piece-driving lever) connected to a standing base (treatment tool-standing piece) through a rotating shaft member (standing piece-driving shaft) by an operation wire (treatment tool-standing operation wire).

SUMMARY OF THE INVENTION

In the treatment tool-standing mechanism using a standing lever that is disclosed in each of JP2010-253234A and JP2002-17663A, a standing lever-receiving chamber, which is a space in which the standing lever is rotatably received and is disposed along the inner surface of a cover member, is provided in the cover member that includes a cylinder covering the outer periphery of the distal-end-portion body as a basic part.

The positions of an observation window and an illumination window, which are disposed in the distal-end-portion body of the endoscope, in the direction of the longitudinal axis of the insertion part are determined on the basis of the positions of the standing base and the standing lever in the direction of the longitudinal axis of the rotating shaft so that a treatment tool led out of the treatment tool outlet through the standing base is displayed in a preferred state in an observation image observed by the observation window.

For this reason, there is a case where a useless space is formed in a region that is close to the proximal end of the observation window and the illumination window and is closer to the distal end than the proximal end of the standing lever-receiving chamber or a region that is close to the distal end of the observation window and the illumination window and is closer to the proximal end than the distal end of the standing lever-receiving chamber.

Accordingly, if the treatment tool-standing mechanism can be adapted so that the useless space is reduced, the length of the distal-end-portion body of the endoscope in the direction of the longitudinal axis of the distal end portion can be shortened and the size of the distal-end-portion body can be reduced.

Therefore, for example, in a case in which the above-mentioned useless space is present on the proximal end side of the observation window and the illumination window, there is considered a method of making the range of the rotatable angle of the standing lever be larger on the distal end side than the proximal end side in a direction perpendicular to the longitudinal axis so that the standing lever-receiving chamber is narrow on the proximal end side of the position of the rotating shaft and is wide on the distal end side thereof.

However, the useless space present on the proximal end side of the observation window and the illumination window can be reduced in this case, but the direction of the standing lever is close to the direction of the longitudinal axis in a state in which the standing lever is rotated to the maximum limit on the distal end side. For this reason, since the inner diameter of the cover member needs to be increased to avoid the interference between the standing lever (standing lever-receiving chamber) and the cover member, an increase in the diameter of the distal-end-portion body is caused.

Accordingly, the size of the distal-end-portion body cannot be reduced in the above-mentioned method.

Further, there is also considered a method of reducing the above-mentioned useless space by shortening the length of the standing lever and making the standing lever-receiving chamber small as a whole.

However, in a case in which the standing lever is made short, a distance between the rotating shaft of the standing lever and a portion of the standing lever, which is connected to the operation wire, is shortened. For this reason, the magnitude of an operating force for rotating the standing lever by an operation for pushing and pulling the operation wire is increased. Accordingly, there is a problem that operability deteriorates.

Furthermore, as the rotatable angle of the standing base is increased to ensure good operability of the standing base, a useless region present on the proximal end side or the distal end side of the observation window and the illumination window is increased or the direction of the standing lever, which is obtained in a case in which the standing lever is rotated to the maximum limit, is close to the direction of the longitudinal axis as described above. Accordingly, there is a problem that an increase in the size of the distal-end-portion body is caused.

The invention has been made in consideration of these circumstances, and an object of the invention is to provide an endoscope and a treatment tool-standing mechanism that allows a distal-end-portion body to be reduced in size while ensuring good operability of a standing base.

In order to achieve the object, an endoscope according to an aspect of the invention comprises: an insertion part that includes a distal end, a proximal end, and a longitudinal axis; a distal-end-portion body that is provided on a distal end side of the insertion part; an operation unit that is provided on a proximal end side of the insertion part; a treatment tool-standing base that is provided in the distal-end-portion body and includes a first rotating shaft; a standing lever that is provided in the distal-end-portion body, includes a second rotating shaft, and allows the treatment tool-standing base to stand and fall; and a transmission member that is provided up to the distal-end-portion body from the operation unit via the insertion part and transmits displacement generated by the operation unit to the standing lever. The standing lever includes a first arm portion that includes a second rotating shaft-connection portion to which the second rotating shaft is connected, a second arm portion that includes a transmission member-connection portion to which the transmission member is connected, and an arm connection portion that is provided between the first and second arm portions. In a case in which a plane, which includes an axis of the second rotating shaft and is parallel to the longitudinal axis, is referred to as a first plane, a plane, which is perpendicular to the axis of the second rotating shaft and crosses the second rotating shaft-connection portion, is referred to as a second plane, a direction, which obliquely crosses the second plane, is referred to as a first direction, and a direction, which includes a component in a direction parallel to the second plane and obliquely crosses the first direction in a case in which the direction is projected onto a first projection plane parallel to the second plane, is referred to as a second direction, the second arm portion and the arm connection portion are disposed on a side opposite to one side of the second plane on which the treatment tool-standing base is provided, the first arm portion is provided along the first direction from the second rotating shaft-connection portion to the arm connection portion, the second arm portion is provided along the second direction from the arm connection portion to the transmission member-connection portion, and the second direction includes a component in a direction opposite to a direction toward the second rotating shaft-connection portion from the arm connection portion in the first projection plane.

According to this aspect, since the standing lever includes the first arm portion and the second arm portion, the standing lever can be easily disposed so as to correspond to the shape of the outer periphery of the distal-end-portion body in a case in which the standing lever is viewed in the direction of the longitudinal axis of the insertion part of the endoscope. Further, since one space of spaces present on the distal end side and the proximal end side of the distal-end-portion body can be reduced depending on the direction of the second arm portion of the standing lever and the other space can be ensured to be wide, a limited space can be effectively used as a whole without an increase in the size of the distal-end-portion body. Furthermore, a distance between a portion of the standing lever, which is connected to the transmission member, and the center of rotation (second rotating shaft) can be set by the first arm portion and the second arm portion so that the magnitude of an operating force for rotating the standing lever is appropriate. Accordingly, it is possible to reduce the size of the distal-end-portion body while ensuring good operability of the standing base.

In an endoscope according to another aspect of the invention, the second direction may be a direction parallel to the second plane.

In another aspect of the invention, the second direction may be a direction obliquely crossing the second plane; in a case in which a plane, which crosses the arm connection portion and is parallel to the second plane, is referred to as a third plane, the transmission member-connection portion may be positioned on a side opposite to one side of the third plane on which the second rotating shaft-connection portion is provided; and an angle between the second direction and the second plane may be smaller than an angle between the first direction and the second plane in a case in which the second direction is projected onto a second projection plane perpendicular to the longitudinal axis.

In another aspect of the invention, the second direction may include a component in a direction toward a distal end side of the longitudinal axis of the insertion part from the arm connection portion in a state in which the first direction is a direction perpendicular to the first plane in the first projection plane.

In another aspect of the invention, the second direction may include a component in a direction toward a proximal end side of the longitudinal axis of the insertion part from the arm connection portion in a state in which the first direction is a direction perpendicular to the first plane in the first projection plane.

In another aspect of the invention, the first and second rotating shafts may be coaxial with each other.

In another aspect of the invention, the distal-end-portion body may include a rotation restricting portion that restricts the range of rotation of the first arm portion about the axis of the second rotating shaft, and the first direction may be a direction perpendicular to the first plane in the first projection plane in a case in which the first arm portion is positioned at a middle position of the range of rotation.

In order to achieve the object, a treatment tool-standing mechanism of an endoscope according to another aspect of the invention includes an insertion part that includes a distal end, a proximal end, and a longitudinal axis, a distal-endportion body that is provided on a distal end side of the insertion part, an operation unit that is provided on a proximal end side of the insertion part, and a treatment tool-standing base that is provided in the distal-end-portion body and includes a first rotating shaft. The treatment tool-standing mechanism comprises: a standing lever that is provided in the distal-end-portion body, includes a second rotating shaft, and allows the treatment tool-standing base to stand and fall; and a transmission member that is provided up to the distal-end-portion body from the operation unit via the insertion part and transmits displacement generated by the operation unit to the standing lever. The standing lever includes a first arm portion that includes a second rotating shaft-connection portion to which the second rotating shaft is connected, a second arm portion that includes a transmission member-connection portion to which the transmission member is connected, and an arm connection portion that is provided between the first and second arm portions. In a case in which a plane, which includes an axis of the second rotating shaft and is parallel to the longitudinal axis, is referred to as a first plane, a plane, which is perpendicular to the axis of the second rotating shaft and crosses the second rotating shaft-connection portion, is referred to as a second plane, a direction, which obliquely crosses the second plane, is referred to as a first direction, and a direction, which includes a component in a direction parallel to the second plane and obliquely crosses the first direction in a case in which the direction is projected onto a first projection plane parallel to the second plane, is referred to as a second direction, the second arm portion and the arm connection portion are disposed on a side opposite to one side of the second plane on which the treatment tool-standing base is provided, the first arm portion is provided along the first direction from the second rotating shaft-connection portion to the arm connection portion, the second arm portion is provided along the second direction from the arm connection portion to the transmission member-connection portion, and the second direction includes a component in a direction opposite to a direction toward the second rotating shaft-connection portion from the arm connection portion in the first projection plane.

According to the invention, it is possible to reduce the size of the distal-end-portion body while ensuring good operability of the standing base.

DESCRIPTION OF THE PREFERRED EMBODIMENTS

Preferred embodiments of the invention will be described in detail below with reference to the accompanying drawings.

Figure 1:
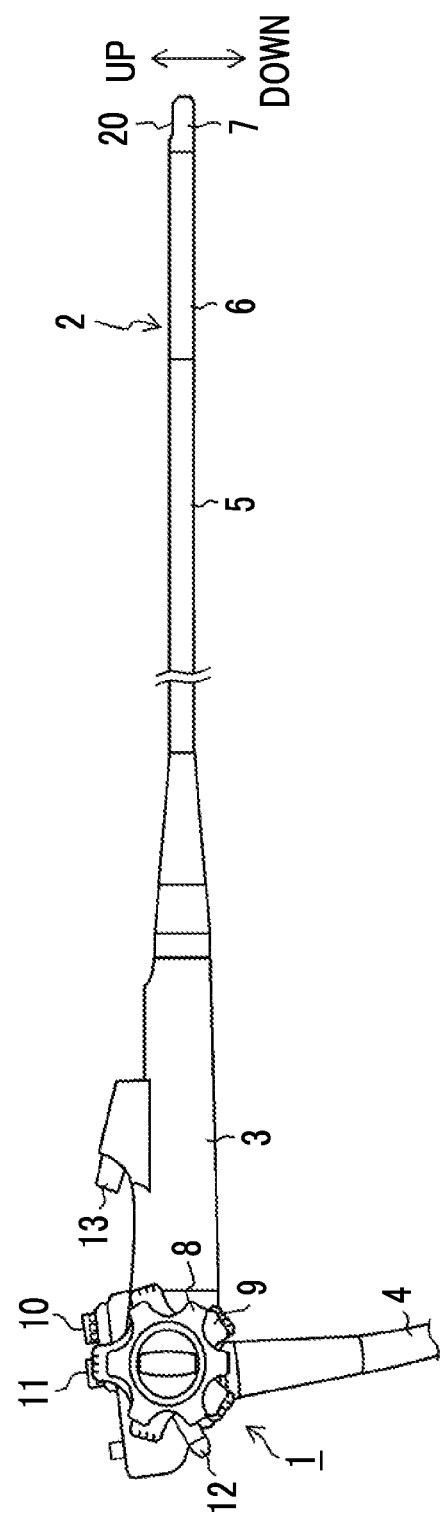
FIG. 1 is a diagram showing the structure of an endoscope according to the invention.

FIG. 1 is a diagram showing the structure of an endoscope 1 according to the invention.

The endoscope 1 shown in FIG. 1 includes: an insertion part 2 that is to be inserted into the body of a patient; an operation unit 3 that is connected to the proximal end of the insertion part 2 and is used for the grip of the endoscope 1, the operation of the insertion part 2, and the like; and a universal cord 4 that connects the endoscope 1 to system components, such as a light source device and a processor device (not shown).

The insertion part 2 includes a soft portion 5, a bendable portion 6, and a distal end portion 7 that are connected in this order from the proximal end toward the distal end. The soft portion 5 has flexibility, and is bent along the insertion path of the insertion part 2 in an arbitrary direction. The bendable portion 6 is vertically and laterally bent by the operation of angle knobs 8 and 9 of the operation unit 3. The distal end portion 7 includes: an observation portion that takes the image of a portion to be observed in the body and sends the taken image to the processor device, which is connected by the universal cord 4, as an observation image (endoscopic image); an illumination portion that irradiates the portion to be observed with illumination light transmitted from the light source device, which is connected by the universal cord 4, through a light guide provided in the endoscope 1; and the like.

Figure 2:
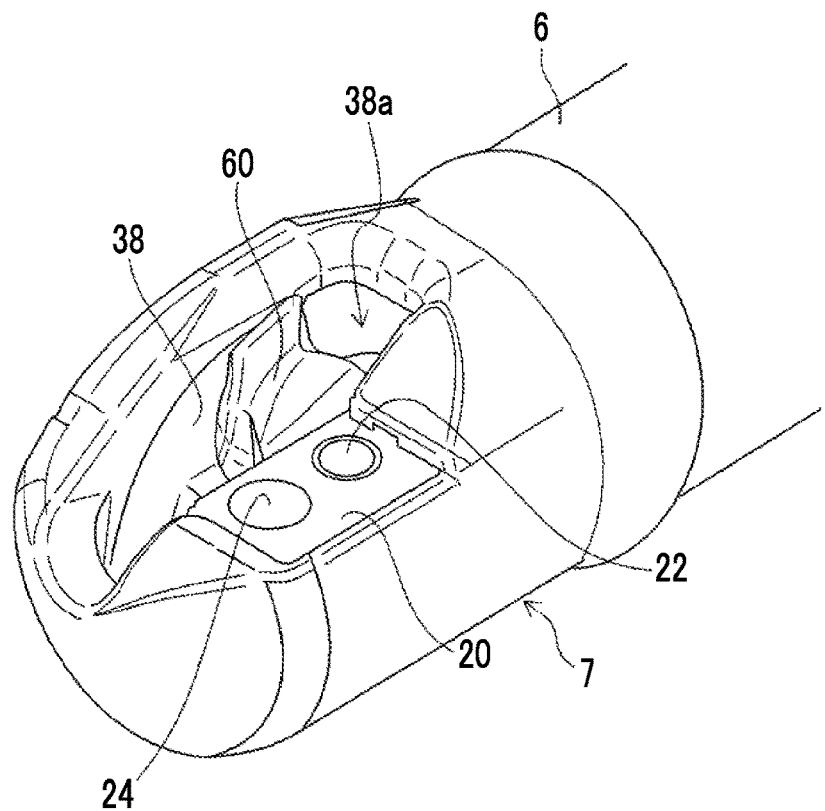
FIG. 2 is an enlarged perspective view of a distal end portion.

FIG. 2 is an enlarged perspective view of the distal end portion 7. The endoscope 1 according to this embodiment is a side-viewing endoscope used as, for example, a duodenoscope and the distal end portion 7 shown in FIG. 2 shows the structure of the side-viewing endoscope.

As shown in FIG. 2, the distal end portion 7 is provided with a flat surface 20 substantially parallel to a longitudinal axis that is the axis of the insertion part 2, and the flat surface 20 is provided with an observation window 22 and an illumination window 24. A longitudinal axis, which is simply mentioned below, means the longitudinal axis of the insertion part 2.

The observation window 22 is a component of the observation portion that acquires the image of a portion to be observed present on the side with respect to the longitudinal axis (in a radial direction), and allows subject light, which is reflected from the portion to be observed present on the side, to be taken into an optical system (an imaging lens and the like) and imaging means that are other components of the observation portion. The illumination window 24 is a component of the illumination portion that is mounted on the distal end portion 7, and irradiates the portion to be observed with illumination light emitted from a light-emitting part which is another component of the illumination portion, that is, a light-emitting part that is provided at a terminal portion of a light guide transmitting light emitted from a light source device.

A position corresponding to the distal end side of the distal end portion 7 in the direction of the longitudinal axis is referred to as a front side (distal end side), a position opposite to the front side (distal end side) is referred to as a rear side (proximal end side), a position facing the flat surface 20 in a direction perpendicular to the flat surface 20 is referred to as an upper side, a position opposite to the upper side is referred to as a lower side (see FIG. 1), and a left side and a right side mean positions corresponding to directions determined on the basis of a positional relationship between the front and the rear and positional relationships between the upper side and the lower side.

Further, a standing base-receiving slit 38 is provided on the right side of the flat surface 20 in the distal end portion 7, and a standing base 60 is provided in the standing base-receiving slit 38. Since the standing base-receiving slit 38 communicates with a treatment tool inlet 13 (see FIG. 1) of the operation unit 3 through a treatment tool-insertion channel inserted into the insertion part 2, a treatment tool inserted from the treatment tool inlet 13 is guided to the standing base-receiving slit 38.

The standing base 60 bends the traveling direction of the treatment tool guided to the standing base-receiving slit 38 to guide the treatment tool in a direction toward an upper opening portion 38a (referred to as a treatment tool outlet 38a) of the standing base-receiving slit 38, and allows the treatment tool to be led out of the treatment tool outlet 38a.

Further, the standing base 60 is allowed to stand or fall (rotated) in a direction where the standing base 60 stands (standing direction) or a direction where the standing base 60 falls (falling direction) by the operation of a standing operation lever 12 (see FIG. 1) of the operation unit 3, and changes the lead-out direction (lead-out angle) of the treatment tool to be led out of the treatment tool outlet 38a.

An air/water supply nozzle (not shown), which can switch the supply of air and the supply of water to the observation window 22 by the operation of an air/water supply button 10 (see FIG. 1) of the operation unit 3, is provided near the observation window 22 of the flat surface 20. Further, since a suction channel is connected to the treatment tool-insertion channel in the insertion part 2, suction from the standing base-receiving slit 38 is performed by the operation of a suction button 11 (see FIG. 1) of the operation unit 3.

Subsequently, a treatment tool-standing mechanism (drive mechanism for the standing base 60) of the distal end portion 7 will be described in detail.

Figure 3:
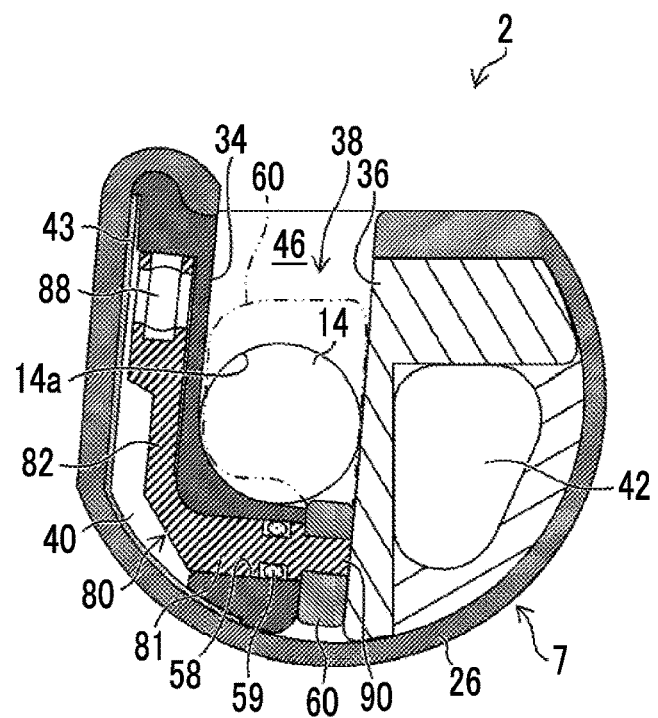
FIG. 3 is a cross-sectional view of the distal end portion.
Figure 4:
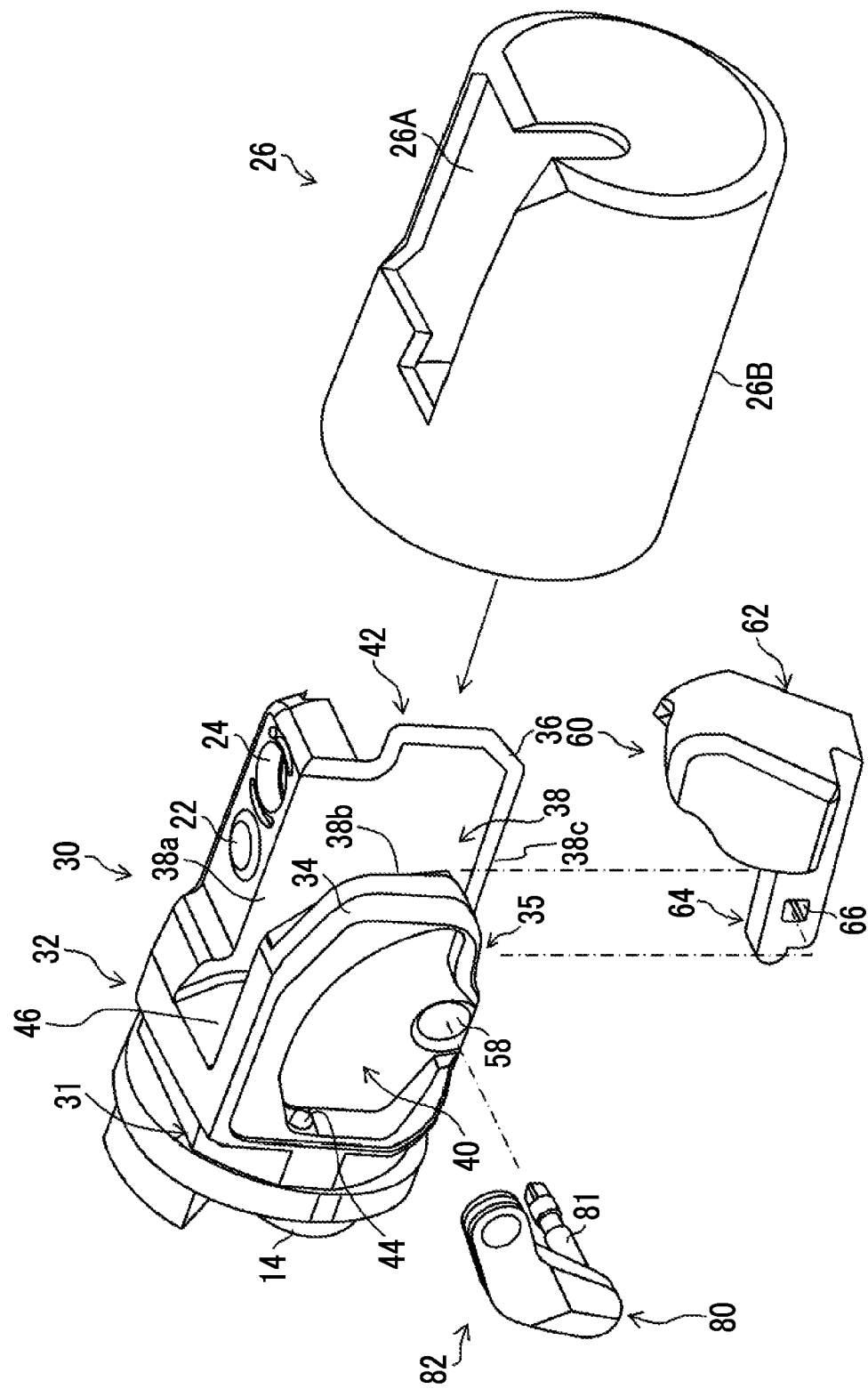
FIG. 4 is an exploded perspective view of the distal end portion.

FIG. 3 is a cross-sectional view of the distal end portion 7 perpendicular to the longitudinal axis, and FIG. 4 is an exploded perspective view of the distal end portion 7.

As shown in FIGS. 3 and 4, the distal end portion 7 includes a distal-end-portion body 30 (see FIG. 4) which partitions the inside of the distal end portion 7 into a plurality of regions and to which various components are integrally assembled, and the outer peripheral portion of the distal-end-portion body 30 is covered with a detachable cap 26.

The cap 26 is made of an elastic material, for example, elastic rubber, and is formed in a shape that has the shape of a cylinder of which the distal end side is closed as a basic shape. The cap 26 includes: an opening window 26A that opens the above-mentioned flat surface 20 and the entire upper opening portion 38a (treatment tool outlet 38a) and a part of the upper side of a front opening portion 38b of the standing base-receiving slit 38; and a partition wall portion 26B that closes the entire lower opening portion 38c and a part of the lower side of the front opening portion 38b of the standing base-receiving slit 38.

Further, an engagement portion (not shown), which protrudes inward in a radial direction in an annular shape, is formed at the proximal end of the cap 26, and the cap 26 is mounted on the distal-end-portion body 30 through the engagement between the engagement portion and a groove 31 formed on the outer peripheral portion of the distal-end-portion body 30. The cap 26 is detached at the time of washing as described below.

The distal-end-portion body 30 is formed of a rigid member that is made of a metal material or the like having corrosion resistance. The distal-end-portion body 30 includes a columnar proximal end portion 32 that is close to the proximal end, and a pair of right and left side wall portions 34 and 36 that extends toward the distal end side from the proximal end portion 32 and faces each other.

Accordingly, in the distal end portion 7, the standing base-receiving slit 38, which is a space portion receiving the standing base 60, is formed between the right side wall portion 34 and the left side wall portion 36, a standing lever-receiving chamber 40, which is a space portion receiving a standing lever 82 of a drive member 80 transmitting a driving force to the standing base 60, is formed on the right side of the side wall portion 34, and an optical-system-receiving chamber 42, which is a space portion receiving components (not shown) of the observation portion and the illumination portion described above, is formed on the left side of the side wall portion 36.

The standing lever-receiving chamber 40 and the optical-system-receiving chamber 42 are covered with a protective plate not shown in FIG. 4 (see a protective plate 43 of the standing lever-receiving chamber 40 in FIG. 3), so that airtightness is kept.

The standing base-receiving slit 38 includes an upper opening portion as the opening portion 38a (treatment tool outlet 38a), includes a front opening portion as the opening portion 38b, and includes a lower opening portion as the opening portion 38c in a state in which the cap 26 is detached from the distal-end-portion body 30 as shown in FIG. 4. These opening portions 38a, 38b, and 38c are connected to each other, so that the standing base-receiving slit 38 extends from an upper surface to a lower surface through a front surface and is opened.

A posterior wall portion 46, which is formed by the proximal end portion 32 of the distal-end-portion body 30, is disposed on the proximal end side of the standing base-receiving slit 38, and an opening portion 14a, which is an pipe-line-end portion of the treatment tool-insertion channel 14, is disposed in the posterior wall portion 46 as shown in FIG. 3.

The standing base 60 is rotatably installed in the standing base-receiving slit 38 as shown in FIG. 4.

Figure 6:
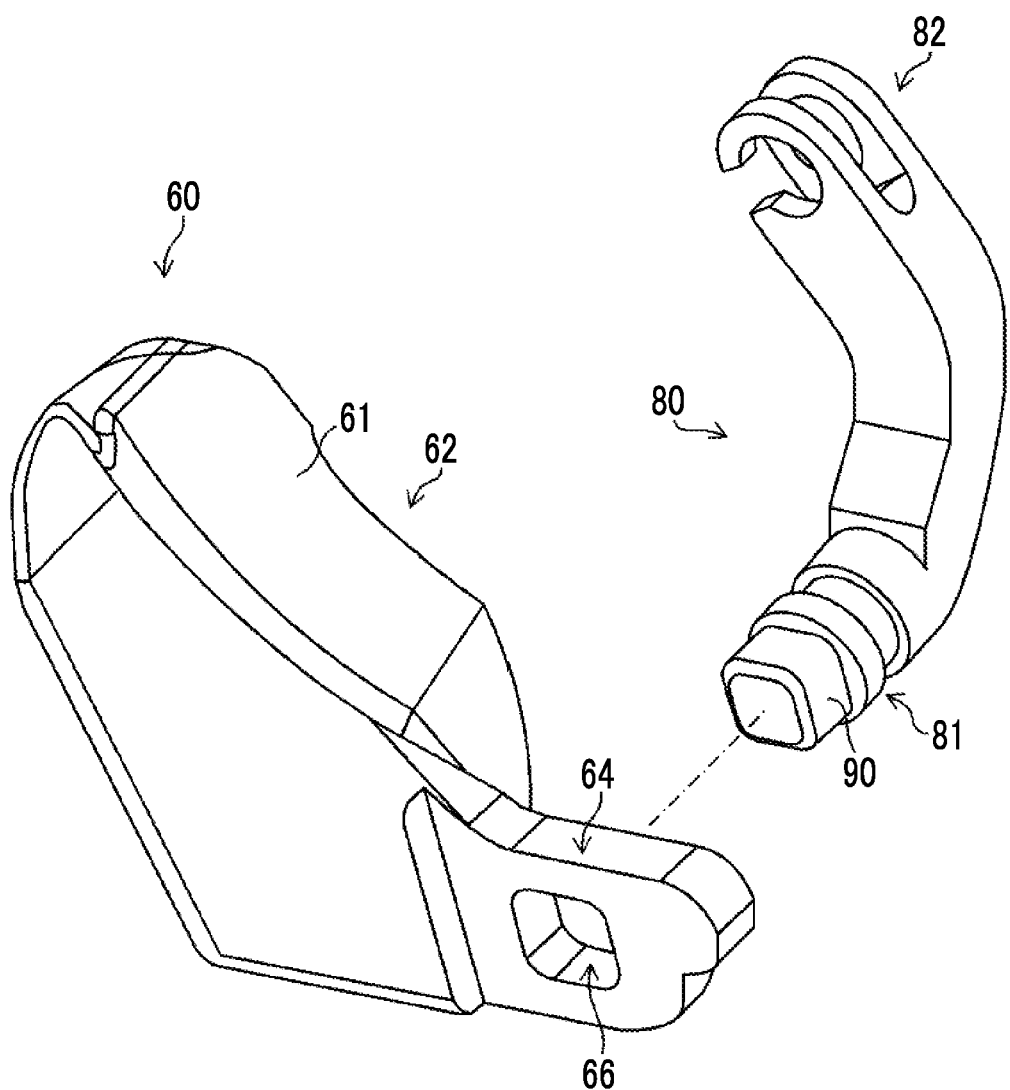
FIG. 6 is a perspective view showing the standing base and the drive member.

As shown in an exploded perspective view of FIG. 6 in which only the standing base 60 and the drive member 80 are shown, the standing base 60 includes a standing base body 62 that includes a guide surface 61 guiding a treatment tool, which is led out of the opening portion 14a of the treatment tool-insertion channel 14, in a direction toward the treatment tool outlet 38a, and a connecting portion 64 that protrudes to the proximal end side from the standing base body 62 and is formed to be narrower than the standing base body 62.

The connecting portion 64 is provided with a rotating-shaft-receiving portion 66 that is to be fixed to a rotating shaft 81 of the drive member 80.

Figure 7:
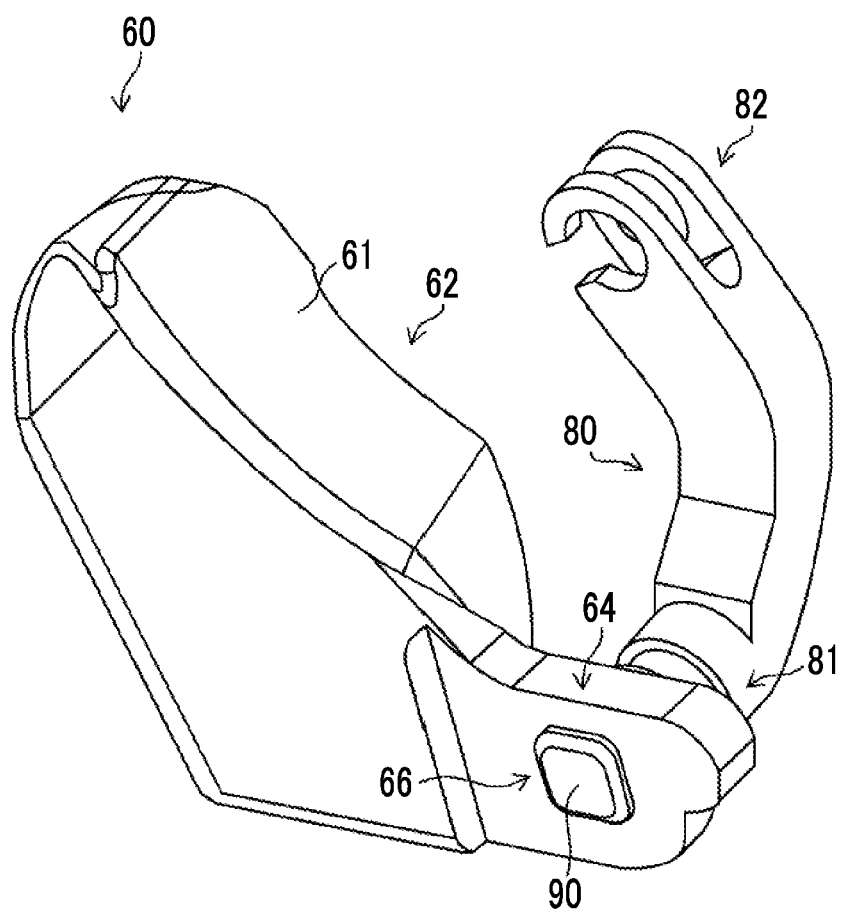
FIG. 7 is a perspective view showing the standing base and the drive member.

The rotating-shaft-receiving portion 66 includes an engagement hole that has a shape and a size substantially corresponding to the shape and the size of an engagement protrusion 90 provided at the distal end of the rotating shaft 81, and the engagement protrusion 90 of the rotating shaft 81 is fitted to the engagement hole as shown in FIG. 7. For example, the engagement protrusion 90 and the engagement hole of the rotating-shaft-receiving portion 66 have a substantially square shape in a cross-section perpendicular to the direction of the axis of the rotating shaft 81.

Since the engagement hole of the rotating-shaft-receiving portion 66 and the engagement protrusion 90 are fitted to each other, the rotating-shaft-receiving portion 66 and the engagement protrusion 90 of the rotating shaft 81 are engaged with each other not to be rotatable relative to each other. Accordingly, the rotating shaft 81 and the standing base 60 are connected to each other in a state in which the rotating shaft 81 and the standing base 60 are rotated while interlocking with each other.

As shown in FIGS. 3 and 4, a holding hole 58, which passes through the distal-end-portion body from the standing lever-receiving chamber 40 to the standing base-receiving slit 38, is formed near the lower end of the side wall portion 34, which is disposed on the right side of the standing base-receiving slit 38, and the rotating shaft 81 of the drive member 80 is rotatably and pivotally supported by the holding hole 58.

The rotating shaft 81 is disposed so that the axis of the rotating shaft 81 (rotation axis 81A to be described) is substantially parallel to a lateral direction at a position below the longitudinal axis serving as the center axis of the insertion part 2.

Since a seal member 59 is disposed between the rotating shaft 81 and the holding hole 58 as shown in FIG. 3, the infiltration of gas and liquid into the standing base-receiving slit 38 and the standing lever-receiving chamber 40 is prevented.

Further, the rotating shaft 81 is disposed so that the engagement protrusion 90, which is one end portion of the rotating shaft 81, protrudes into the standing base-receiving slit 38, and is connected to the standing base 60 as described above. A portion of the side wall portion 34 at which the holding hole 58 is formed protrudes so as to close to the side wall portion 36, and the engagement protrusion 90 of the rotating shaft 81 is disposed so as to protrude at a portion where a gap between the side wall portions 34 and 36 is small.

The standing lever-receiving chamber 40, which is formed on the right side of the side wall portion 34, is a space portion in which the standing lever 82 of the drive member 80 is received so as to be rotationally movable about the holding hole 58 as shown in FIG. 4.

Figure 5:
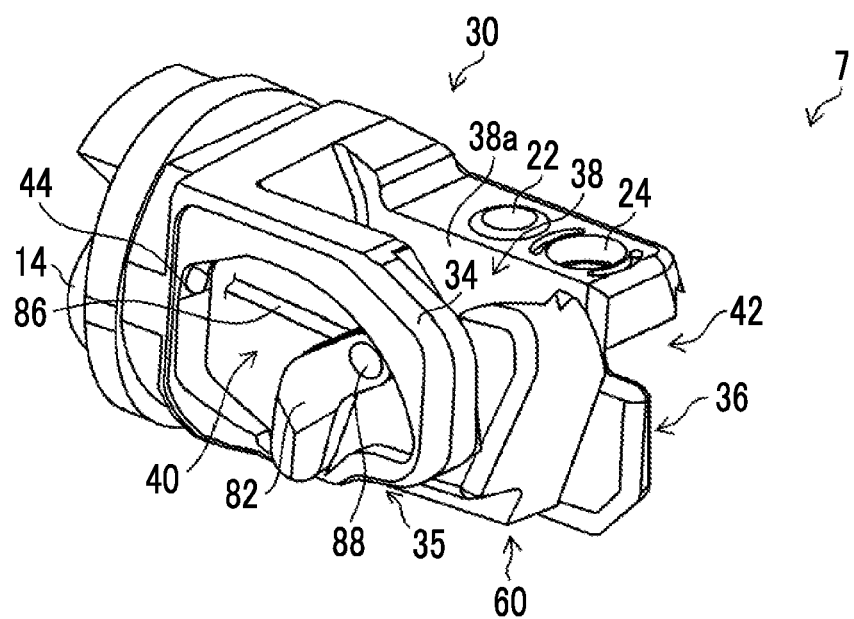
FIG. 5 is a perspective view showing a state in which a standing base and a drive member are assembled to a distal-end-portion body.

In this embodiment, the standing lever 82 and the rotating shaft 81 are integrally formed as the drive member 80 as shown in FIGS. 4, 6, and 7 and the rotating shaft 81 of the drive member 80 is disposed so as to be inserted into the holding hole 58. Accordingly, the standing lever 82 is disposed so as to be received in the standing lever-receiving chamber 40 as shown in FIGS. 3 and 5. FIG. 5 is a perspective view showing a state in which the standing base 60 and the drive member 80 are assembled to the distal-end-portion body 30.

One end portion (proximal end portion) of the standing lever 82 is connected to the rotating shaft 81, and the standing lever 82 extends in a longitudinal shape from one end portion thereof to the other end portion (distal end portion) thereof that is spaced apart from one end portion thereof in a direction perpendicular to the axis of the rotating shaft 81. The shape and the like of the standing lever 82 will be described in detail later.

As shown in FIG. 5, the distal end portion of an operation wire 86 is connected to the distal end portion of the standing lever 82 through a connector 88. The operation wire 86 is inserted into the insertion part 2 from a wire insertion hole 44, which is opened to the wall surface of the standing lever-receiving chamber 40, and is connected to the standing operation lever 12 of the operation unit 3.

Accordingly, the operation wire 86 is pushed and pulled by the operation of the standing operation lever 12, so that the standing lever 82 is rotated together with the rotating shaft 81. Further, the standing base 60 is rotated by the rotation of the rotating shaft 81, so that the standing base 60 is allowed to stand and fall.

The structure of the rotating shaft 81, which connects the standing lever 82 to the standing base 60, is not limited to this embodiment. For example, the standing base 60 may include a first rotating shaft, the standing lever 82 may include a second rotating shaft, and the first and second rotating shafts may be integrated with each other or connected to each other. The rotating shaft 81 of this embodiment corresponds to the first rotating shaft or the second rotating shaft in a case in which the first and second rotating shafts are integrated with each other. Further, the rotating shaft 81 of this embodiment corresponds to an aspect in which the first and second rotating shafts are coaxial with each other, but the first and second rotating shafts may not be coaxial with each other.

Furthermore, the operation wire 86 is one aspect of a transmission member that is provided up to the distal-end-portion body 30 from the operation unit 3 via the insertion part 2 and transmits displacement generated by the operation unit 3 to the standing lever 82, and a mechanism for rotating the standing lever 82 is not limited to this embodiment in which the standing lever 82 is pushed and pulled by the operation wire 86.

Subsequently, the shape of the standing lever 82 of the drive member 80 and the shape of the standing lever-receiving chamber 40 will be described in detail.

Figure 8:
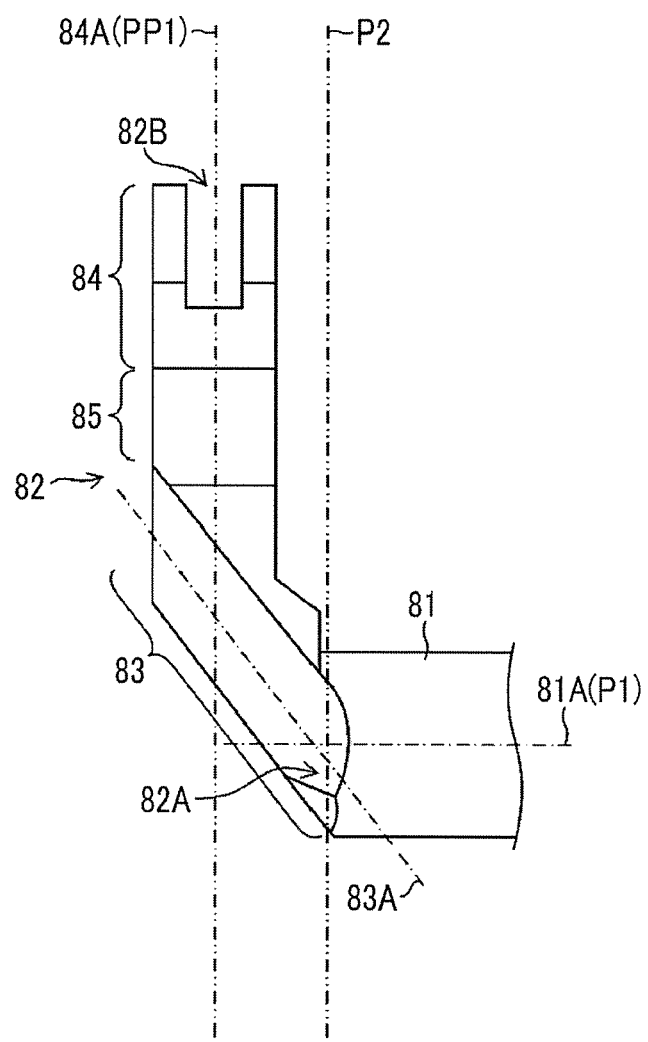
FIG. 8 is a front view showing only the drive member of the distal end portion.
Figure 9:
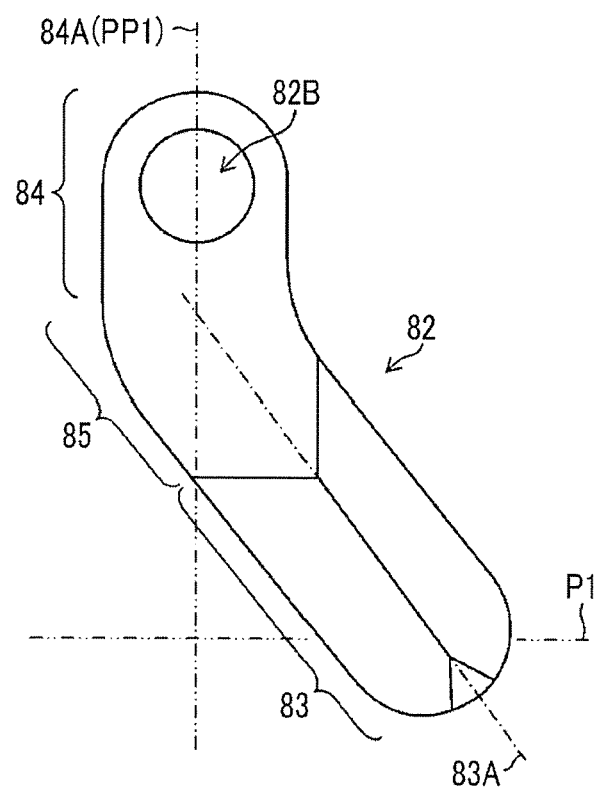
FIG. 9 is a side view showing only the drive member of the distal end portion.
Figure 10:
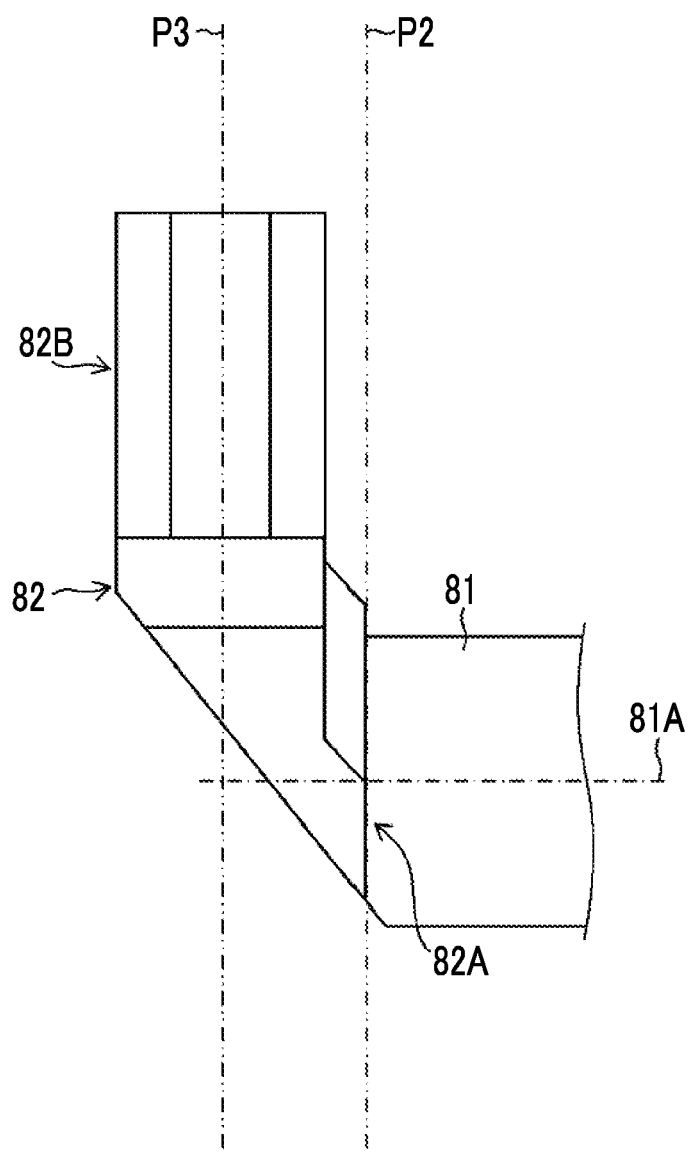
FIG. 10 is a plan view showing only the drive member of the distal end portion.
Figure 11:
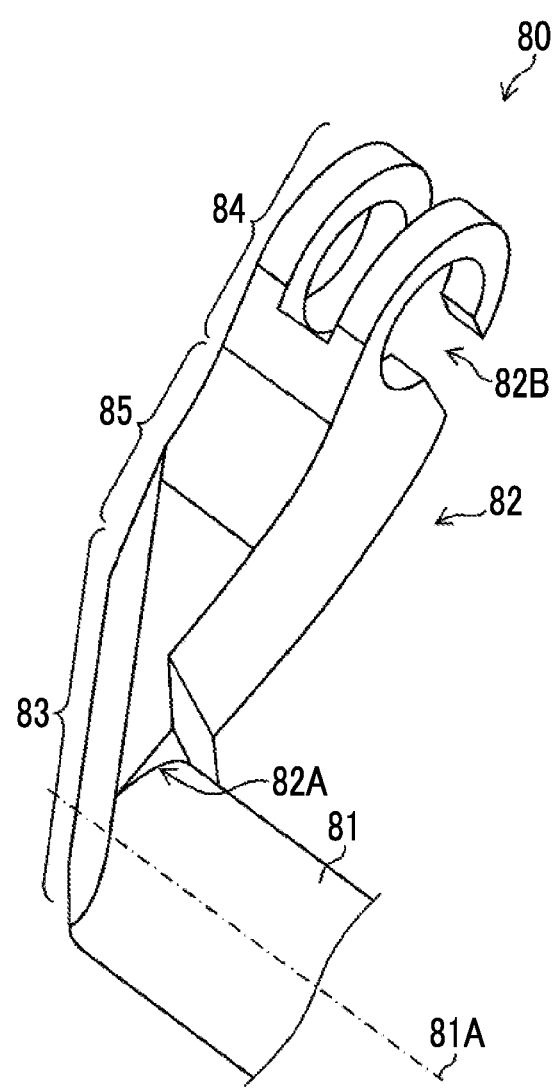
FIG. 11 is a perspective view showing only the drive member of the distal end portion.

FIG. 8 is a front view showing only the drive member 80 of the distal end portion 7 (a diagram viewed from the front side of the distal end portion 7), FIG. 9 is a side view showing only the drive member 80 of the distal end portion 7 (a diagram viewed from the right side of the distal end portion 7), FIG. 10 is a plan view showing only the drive member 80 of the distal end portion 7 (a diagram viewed from the upper side of the distal end portion 7), and FIG. 11 is a perspective view showing only the drive member 80 of the distal end portion 7.

As shown in FIGS. 8, 9, 10, and 11, the drive member 80 is composed of the rotating shaft 81 and the standing lever 82 having described above, and the rotating shaft 81 is formed in a columnar shape along the axis 81A. Further, the axis 81A of the rotating shaft 81 is disposed below the longitudinal axis in the distal end portion 7 so as to be substantially parallel to the lateral direction as described above. In the following description, the axis 81A of the rotating shaft 81, that is, an axis serving as the center of rotation of the standing lever 82 (drive member 80) is referred to as the rotation axis 81A.

The standing lever 82 is formed in a longitudinal shape in which a distal end is bent, and includes a rotating shaft-connection portion 82A which is provided at one end portion (proximal end portion) of the standing lever 82 and to which the rotating shaft 81 corresponding to the second rotating shaft is connected, and a wire-connection portion 82B which is provided at the other end portion (distal end portion) of the standing lever 82 and to which the operation wire 86 corresponding to the transmission member is connected through the above-mentioned connector 88 or the like. The rotating shaft-connection portion 82A corresponds to a second rotating shaft-connection portion to which the second rotating shaft is connected, and the wire-connection portion 82B corresponds to a transmission member-connection portion to which the transmission member is connected.

Further, the standing lever 82 includes a first arm portion 83 that includes the rotating shaft-connection portion 82A, a second arm portion 84 that includes the wire-connection portion 82B, and an arm connection portion 85 that is provided between the first and second arm portions 83 and 84.

The first arm portion 83 extends to the arm connection portion 85 from an end portion of the rotating shaft 81, and is provided along a first axis 83A extending in a first direction that is different from the direction of the axis 81A of the rotating shaft 81, that is, the rotation axis 81A (see FIG. 8).

Further, the second arm portion 84 extends from the arm connection portion 85, and is provided along a second axis 84A extending in a second direction that is not parallel to a plane including the rotation axis 81A and the first axis 83A.

That is, a plane, which includes the axis 81A of the rotating shaft 81 (rotation axis 81A) and is parallel to the longitudinal axis of the insertion part 2, is referred to as a first plane P1; a plane, which is perpendicular to the rotation axis 81A and crosses the rotating shaft-connection portion 82A, is referred to as a second plane P2; a direction, which obliquely crosses the second plane P2, is referred to as a first direction; and a direction, which includes a component in a direction parallel to the second plane P2 and obliquely crosses the first direction in a case in which the direction is projected onto a first projection plane PP1 parallel to the second plane P2, is referred to as a second direction.

Further, the second direction includes a component in a direction opposite to the direction toward the rotating shaft-connection portion 82A from the arm connection portion 85 in the first projection plane PP1 parallel to the second plane P2.

In this case, the second arm portion 84 and the arm connection portion 85 are disposed on a side opposite to one side of the second plane P2 on which the standing base 60 is provided. The first arm portion 83 is provided along the first direction from the rotating shaft-connection portion 82A to the arm connection portion 85. The second arm portion 84 is provided along the second direction from the arm connection portion 85 to the wire-connection portion 82B.

In this embodiment, the second direction is parallel to the second plane P2.

Figure 12:
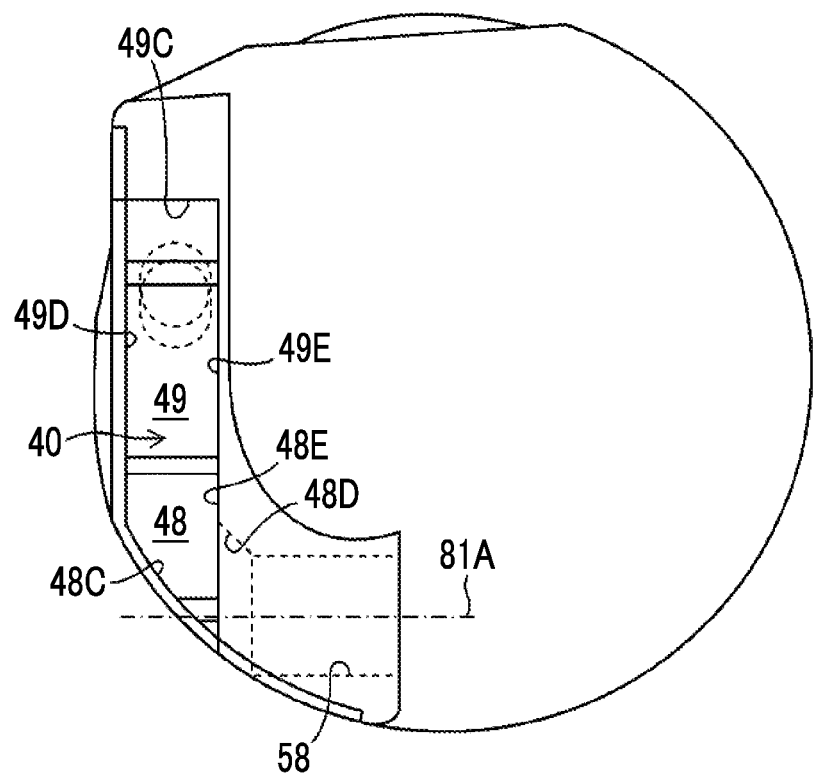
FIG. 12 is a front view of a standing lever-receiving chamber that is formed in a side wall portion of the distal-end-portion body.
Figure 13:
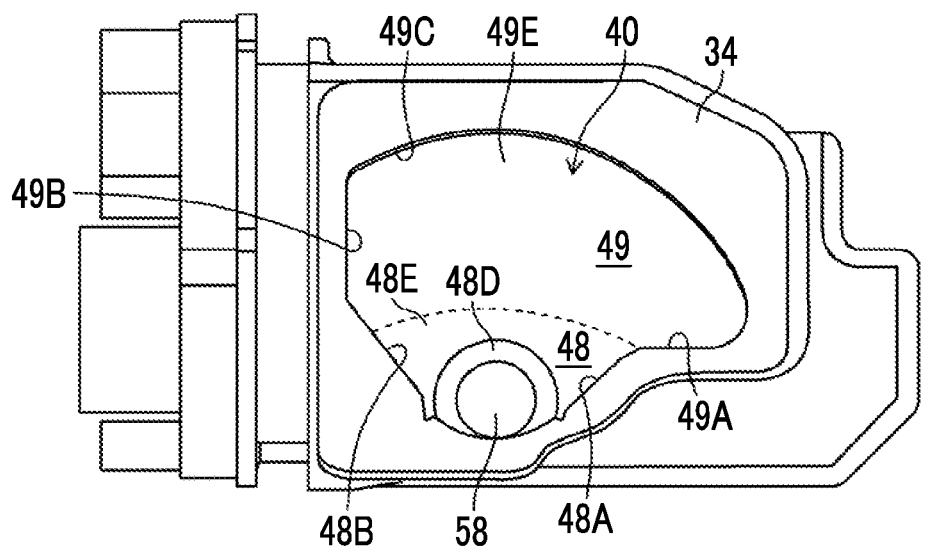
FIG. 13 is a side view of the standing lever-receiving chamber that is formed in the side wall portion of the distal-end-portion body.

FIG. 12 is a front view of the standing lever-receiving chamber 40 that is formed in the side wall portion 34 of the distal-end-portion body 30, and FIG. 13 is a side view of the standing lever-receiving chamber 40 that is formed in the side wall portion 34 of the distal-end-portion body 30.

As shown in FIGS. 12 and 13, the standing lever-receiving chamber 40 is formed so as to communicate with the holding hole 58 into which the rotating shaft 81 of the drive member 80 is inserted and disposed. The standing lever-receiving chamber 40 includes a first arm receiving portion 48 in which the second arm portion 84 is mainly received so as to be rotatable about the axis 81A of the rotating shaft 81 (rotation axis 81A), and a second arm receiving portion 49 in which the first arm portion 83 is mainly received so as to be rotatable about the rotation axis 81A.

In a case in which the first arm receiving portion 48 is viewed from the side of the distal end portion 7 as shown in FIG. 13, the first arm receiving portion 48 includes a region having the shape of a profile along the shape of a fan having a center at the position of the end portion of the holding hole 58, that is, the position of the proximal end at which the rotating shaft-connection portion 82A of the standing lever 82 received in the standing lever-receiving chamber 40 is disposed.

The first arm receiving portion 48 includes a distal end-side end surface 48A and a proximal end-side end surface 48B as inner wall surfaces that partition the first arm receiving portion 48, that is, inner wall surfaces of the standing lever-receiving chamber 40 disposed along the positions of the first arm portion 83 in cases in which the standing lever 82 is rotated to the maximum limits of the distal end side (front side) and the proximal end side (rear side) of the distal end portion 7.

The distal end-side end surface 48A and the proximal end-side end surface 48B are formed along straight lines that are substantially orthogonal to each other. The distal end-side end surface 48A and the proximal end-side end surface 48B have an inclination angle of about 45° with respect to a vertical direction on the distal end side and the proximal end side, respectively.

Here, the inner wall surface, which is formed on one side of the standing lever 82 received in the standing lever-receiving chamber 40 and is close to the standing base 60, of the inner wall surfaces defining the standing lever-receiving chamber 40 is referred to as an inside inner wall surface, and the inner wall surface opposite thereto is referred to as an outside inner wall surface. The outside inner wall surface is formed by the protective plate 43 that covers the standing lever-receiving chamber 40 as described above. Likewise, the outer surface, which is formed on one side close to the standing base 60, of outer surfaces, which form the standing lever 82, is referred to as an inside outer surface, and the outer surface opposite thereto is referred to as an outside outer surface.

In a case in which the first arm receiving portion 48 is viewed from the front side of the distal end portion 7 as shown in FIG. 12, the first arm receiving portion 48 includes an inclined surface 48C, which is parallel to the longitudinal axis of the insertion part 2 and obliquely crosses the rotation axis 81A (lateral direction), as the outside inner wall surface of the standing lever-receiving chamber 40.

Further, the first arm receiving portion 48 includes a conical tapered surface 48D along which the inside outer surface of the first arm portion 83 is formed at the peripheral portion of the end portion of the holding hole 58 as the inside inner wall surface of the standing lever-receiving chamber 40, and includes a vertical surface 48E that is provided near the tapered surface 48D and is substantially perpendicular to the rotation axis 81A.

In a case in which the distal end portion 7 is viewed from the side as shown in FIG. 13, the second arm receiving portion 49 includes a region that is further spaced apart from the position of the end portion of the holding hole 58 than the first arm receiving portion 48 and is connected to the first arm receiving portion 48.

Further, the second arm receiving portion 49 includes an upper inner wall surface 49C of the standing lever-receiving chamber 40 that is an inner wall surface partitioning the second arm receiving portion 49 and is formed in an arc shape, and a distal end-side end surface 49A and a proximal end-side end surface 49B as inner wall surfaces of the standing lever-receiving chamber 40 disposed along the positions of the second arm portion 84 in cases in which the standing lever 82 is rotated to the maximum limits of the distal end side and the proximal end side of the distal end portion 7.

The distal end-side end surface 49A is connected to the distal end-side end surface 48A of the first arm receiving portion 48, and is formed along a straight line substantially parallel to the longitudinal axis of the insertion part 2.

The proximal end-side end surface 49B is connected to the proximal end-side end surface 48B of the first arm receiving portion 48, and is formed along a vertical direction.

Further, in a case in which the second arm receiving portion 49 is viewed from the front side of the distal end portion 7 as shown in FIG. 12, the second arm receiving portion 49 includes vertical surfaces 49D and 49E substantially perpendicular to the rotation axis 81A as the outside inner wall surface and the inside inner wall surface of the standing lever-receiving chamber 40.

The vertical surface 49D is connected to the inclined surface 48C of the first arm receiving portion 48, and the vertical surface 49E is connected to the vertical surface 48E of the first arm receiving portion 48.

An action and an effect, which are obtained from the treatment tool-standing mechanism provided in the distal end portion 7 as described above, will be described.

According to the treatment tool-standing mechanism of this embodiment, the first arm portion 83 of the standing lever 82 of the drive member 80 extends in the first direction obliquely crossing the second plane P2 perpendicular to the rotation axis 81A as described above. For this reason, as shown in FIGS. 3 and 12, the outside inner wall surface of the first arm receiving portion 48 of the standing lever-receiving chamber 40 can be formed of the inclined surface 48C.

Accordingly, since the standing lever-receiving chamber 40 can be disposed along the curved inner surface of the cap 26, a useless space between the standing lever-receiving chamber 40 (protective plate 43) and the inner surface of the cap 26 can be reduced. Accordingly, since the inner diameter of the cap 26 can be reduced, the diameter of the distal end portion 7 can be reduced.

Further, according to the treatment tool-standing mechanism of this embodiment, the following action and effect are obtained.

Figure 14:
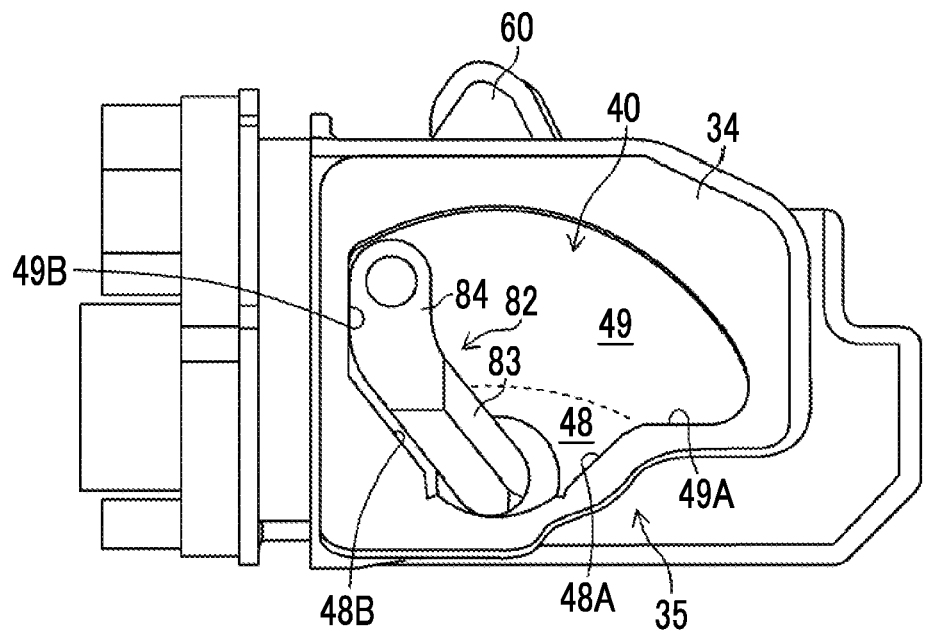
FIG. 14 is a side view showing the state of a standing lever in the standing lever-receiving chamber in a case in which the standing base is allowed to stand most.
Figure 15:
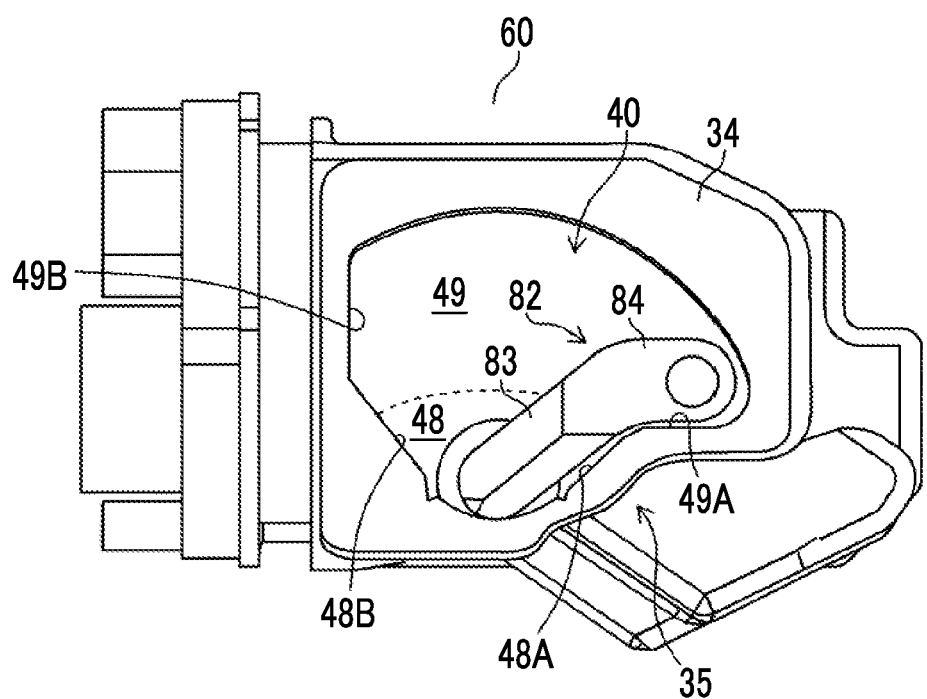
FIG. 15 is a side view showing the state of the standing lever in the standing lever-receiving chamber in a case in which the standing base is allowed to fall most.

FIGS. 14 and 15 are side views showing the distal-end-portion body 30, to which the standing base 60 and the drive member 80 are assembled, from the right side surface of the distal-end-portion body 30. FIG. 14 shows a state in which the standing lever 82 is rotated to the maximum limit on the proximal end side of the distal end portion 7 in the standing lever-receiving chamber 40 (a state in which the standing base 60 is allowed to stand most), and FIG. 15 shows a state in which the standing lever 82 is rotated to the maximum limit on the distal end side of the distal end portion 7 in the standing lever-receiving chamber 40 (a state in which the standing base 60 is allowed to fall most).

In a state in which the standing lever 82 is rotated to the maximum limit on the proximal end side of the distal end portion 7 in the standing lever-receiving chamber 40 as shown in FIG. 14, the first arm portion 83 of the standing lever 82 is in contact with or close to the proximal end-side end surface 48B of the first arm receiving portion 48 and the second arm portion 84 is in contact with or close to the proximal end-side end surface 49B of the second arm receiving portion 49.

Further, in a state in which the standing lever 82 is rotated to the maximum limit on the distal end side of the distal end portion 7 in the standing lever-receiving chamber 40 as shown in FIG. 15, the first arm portion 83 of the standing lever 82 is in contact with or close to the distal end-side end surface 48A of the first arm receiving portion 48 and the second arm portion 84 is in contact with or close to the distal end-side end surface 49A of the second arm receiving portion 49.

In this embodiment, the second arm portion 84 of the standing lever 82 is in contact with the proximal end-side end surface 49B and the distal end-side end surface 49A as shown in FIGS. 14 and 15. However, any one of the first and second arm portions 83 and 84 may be in contact with any one of the proximal end-side end surface 48B and the proximal end-side end surface 49B and any one of the distal end-side end surface 48A and the distal end-side end surface 49A.

Figure 16:
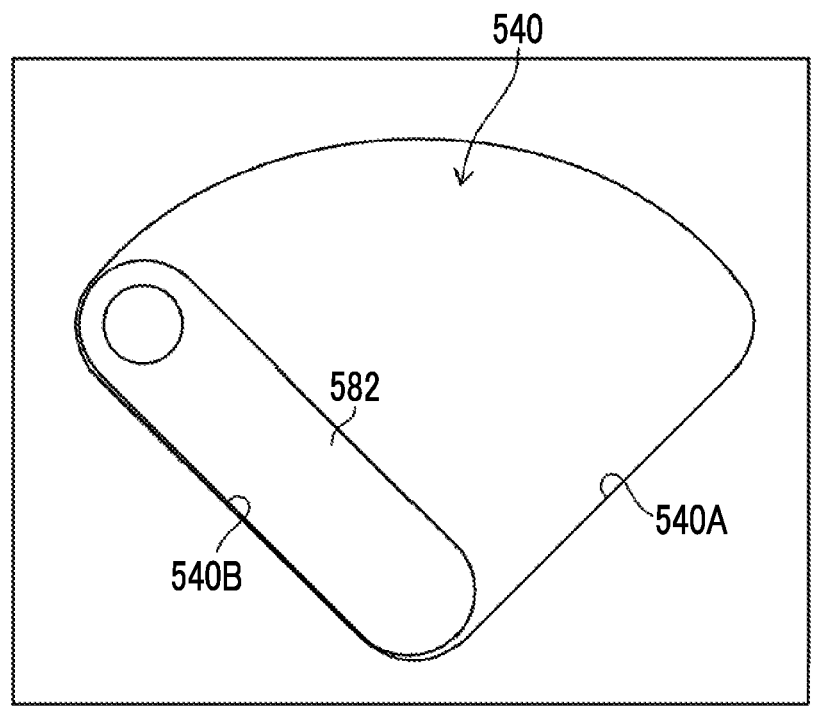
FIG. 16 is a side view showing a standing lever and a standing lever-receiving chamber of a reference form and is a side view showing the state of the standing lever in the standing lever-receiving chamber in a case in which the standing base is allowed to stand most.
Figure 17:
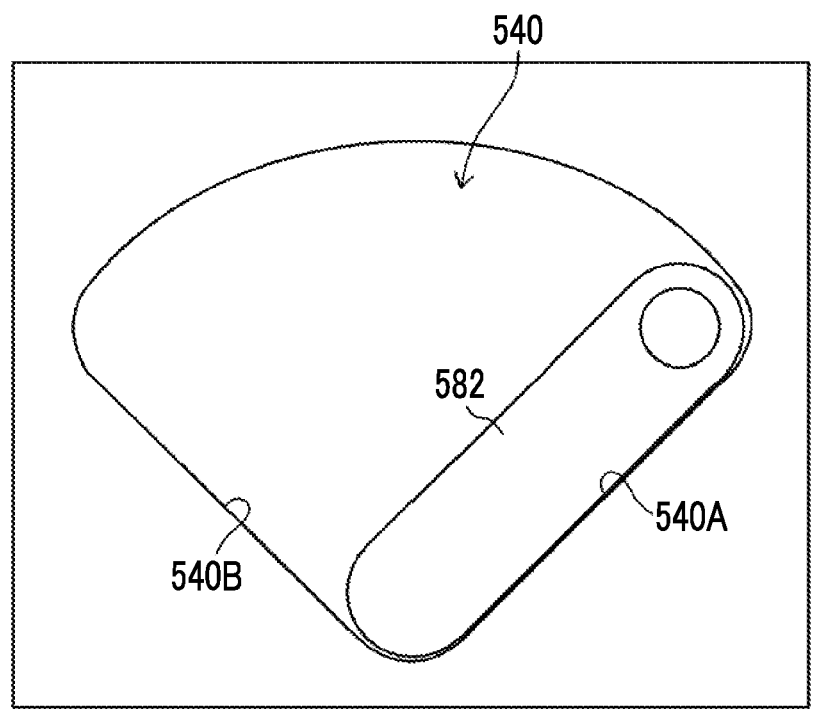
FIG. 17 is a side view showing the standing lever and the standing lever-receiving chamber of the reference form and is a side view showing the state of the standing lever in the standing lever-receiving chamber in a case in which the standing base is allowed to fall most.

FIGS. 16 and 17 are side views showing a standing lever 582 and a standing lever-receiving chamber 540 of a reference form that are to be compared with the standing lever 82 and the standing lever-receiving chamber 40 of this embodiment, FIG. 16 shows a state in which the standing lever 582 is rotated to the maximum limit on the proximal end side of the distal end portion 7 in the standing lever-receiving chamber 540 (a state in which the standing base 60 is allowed to stand most), and FIG. 17 shows a state in which the standing lever 582 is rotated to the maximum limit on the distal end side of the distal end portion 7 in the standing lever-receiving chamber 540 (a state in which the standing base 60 is allowed to fall most).

In comparison with the standing lever 82 of this embodiment, the standing lever 582 of the reference form shown in FIGS. 16 and 17 is formed in the shape of a straight line as a whole in a case in which the standing lever 582 is viewed from the side. The standing lever 582 corresponds to an aspect in which the first and second arm portions 83 and 84 are formed along the same direction in a case in which the standing lever 82 is projected onto a plane perpendicular to the rotation axis 81A in this embodiment. Components of the distal end portion 7 other than the standing lever 582 and the standing lever-receiving chamber 540 are the same as those of this embodiment, and will be denoted by the same reference numerals as the reference numerals of this embodiment.

The standing lever-receiving chamber 540 has the shape of a fan, which has a center at the position of the proximal end at which a rotating shaft-connection portion 82A of the standing lever 582 is disposed, as a whole. The standing lever-receiving chamber 540 includes a distal end-side end surface 540A and a proximal end-side end surface 540B as inner wall surfaces of the standing lever-receiving chamber 540 that restrict the range of rotation of the standing lever 582 about the rotation axis 81A to the distal end side and the proximal end side of the distal end portion 7.

The distal end-side end surface 540A and the proximal end-side end surface 540B are formed along straight lines that are substantially orthogonal to each other as in the case of the distal end-side end surface 48A and the proximal end-side end surface 48B of this embodiment. The distal end-side end surface 540A and the proximal end-side end surface 540B have an inclination angle of about 45° with respect to a vertical direction on the distal end side and the proximal end side, respectively.

As understood from the comparison between FIGS. 16 and 17 of the reference form and FIGS. 14 and 15 of this embodiment, in this embodiment and the reference form, the rotatable angle of the standing lever 82 is the same as the rotatable angle of the standing lever 582 (about) 90° and the length of the range of the standing lever-receiving chamber 40 in a front-rear direction (the direction of the longitudinal axis of the insertion part 2) substantially corresponds to the length of the range of the standing lever-receiving chamber 540 in the front-rear direction.

Further, in this embodiment and the reference form, a distance between the rotation axis 81A and a portion of the standing lever 82, which is connected to the operation wire 86, (wire-connection portion 82B) is substantially equal to a distance between the rotation axis 81A and a portion of the standing lever 582, which is connected to the operation wire 86, and the magnitude of an operating force for rotating the standing lever 82 by an operation for pushing and pulling the operation wire 86 is substantially equal to the magnitude of an operating force for rotating the standing lever 582 by an operation for pushing and pulling the operation wire 86. Accordingly, the operability of the standing base 60 in this embodiment is substantially the same as the operability of the standing base 60 in the reference form.

In contrast, the position of the rotation axis 81A in the front-rear direction in the range of the standing lever-receiving chamber 40 in the front-rear direction in this embodiment is disposed closer to the rear side (proximal end side) than that in the reference form.

The positions of the observation window 22 and the illumination window 24 of the distal end portion 7 in the front-rear direction are determined on the basis of a positional relationship between the rotation axis 81A and themselves so that a treatment tool led out of the treatment tool outlet 38a through the standing base 60 is displayed in a preferred state in an observation image observed by the observation window 22. For this reason, there is a case where a useless space is formed in a region that is close to the proximal end of the observation window 22 and the illumination window 24 and is closer to the distal end than the proximal end of the standing lever-receiving chamber 40.

In this case, since the rotation axis 81A is disposed close to the proximal end in the range of the standing lever-receiving chamber 40 in the front-rear direction as in this embodiment, the useless space can be reduced. Accordingly, the length of the distal end portion 7 in the front-rear direction (the direction of the longitudinal axis of the distal end portion 7) can be shortened.

Figure 18:
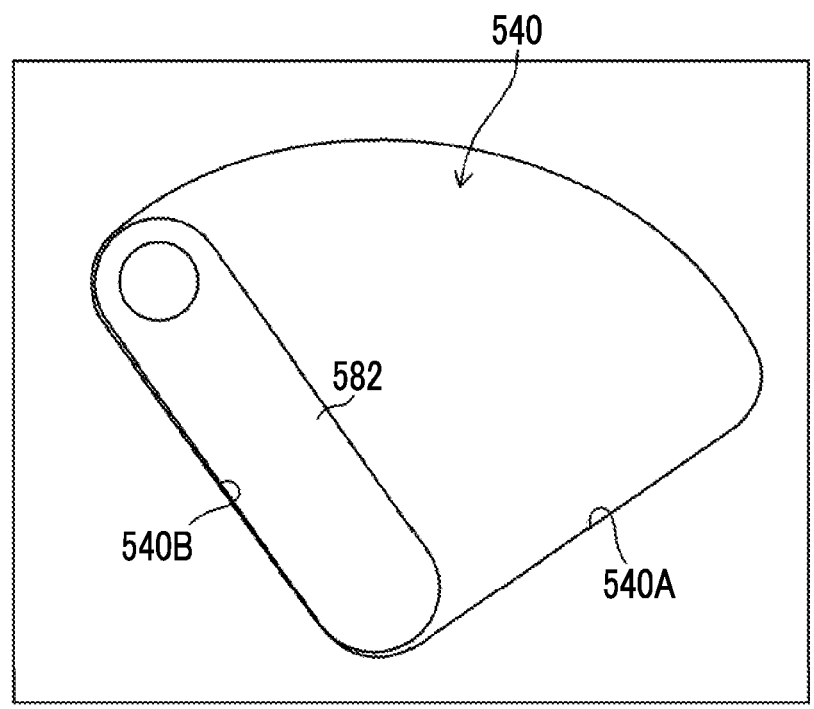
FIG. 18 is a side view showing another form of the standing lever-receiving chamber of the reference form of FIGS. 16 and 17.

Further, in a case in which an inclination angle of the distal end-side end surface 540A with respect to the vertical direction on the distal end side is set to be larger than an inclination angle of the proximal end-side end surface 540B with respect to the vertical direction on the proximal end side as shown in FIG. 18 in regard to the standing lever-receiving chamber 540 for the standing lever 582 shown in FIGS. 16 and 17, the rotation axis 81A can be disposed close to the proximal end side in the range of the standing lever-receiving chamber 540 in the front-rear direction as in this embodiment. Accordingly, the above-mentioned useless space can be reduced.

Figure 19:
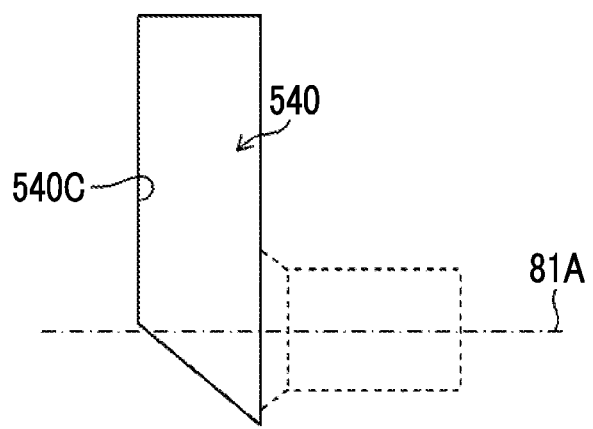
FIG. 19 is a front view of the standing lever-receiving chamber of FIG. 18.

However, in this case, as shown in the front view of the standing lever-receiving chamber 540 of FIG. 19, the range of a vertical surface 540C substantially orthogonal to the rotation axis 81A on the outside inner wall surface of the standing lever-receiving chamber 540 is widened downward in comparison with the vertical surface 49D (see FIG. 12) of this embodiment corresponding to the vertical surface 540C. For this reason, since the inner diameter of the cap 26 needs to be increased in the reference form shown in FIGS. 16 and 17, the diameter of the distal end portion 7 is increased.

Further, in the reference form shown in FIGS. 16 and 17, the inclination angle of the distal end-side end surface 540A of the standing lever-receiving chamber 540 with respect to the vertical direction needs to be reduced to avoid an increase in the diameter of the distal end portion 7. For this reason, the rotatable angle of the standing lever 582 is reduced.

That is, according to the treatment tool-standing mechanism of this embodiment, the rotation angle of the standing lever 82 can be increased without causing an increase in the diameter of the distal end portion 7.

Further, according to the drive of the standing base 60 of this embodiment, as in the case of a notch portion 35 shown in FIGS. 13 to 15, the lower portion of the distal end portion of the side wall portion 34 can be formed in a notched shape so as to correspond to the shape of a bent profile, which is formed by the distal end-side end surface 48A and the distal end-side end surface 49A of the standing lever-receiving chamber 40.

For this reason, in a case in which the cap 26 is detached from the distal-end-portion body 30 and the washing of the standing base 60 and the like are to be performed, the standing base 60 is allowed to fall most as shown in FIG. 15, so that a large area of the standing base 60 can be exposed from the standing base-receiving slit 38. Accordingly, an effect of easily washing the standing base 60 is also obtained.

In the embodiment, the second arm portion 84 of the standing lever 82 of the drive member 80 extends from the arm connection portion 85 along the second direction, and the second direction is parallel to the second plane P2 (see FIGS. 8 and 9, and the like). However, as long as the second direction is a direction that includes a component in a direction parallel to the second plane P2 and obliquely crosses the first direction (a direction in which the first arm portion 83 extends) in a case in which the direction is projected onto a first projection plane PP1 parallel to the second plane P2, the second direction may not be parallel to the second plane P2.

For example, the second direction may be a direction that obliquely crosses the second plane P2 and allows the wire-connection portion 82B to be positioned on one side of a third plane P3 opposite to the side on which the rotating shaft-connection portion 82A is provided in a case in which a plane, which crosses the arm connection portion 85 and is parallel to the second plane P2, is referred to as the third plane P3 (see FIG. 10).

In this case, it is preferable that an angle between the second direction and the second plane is smaller than an angle between the first direction and the second plane in a case in which the second direction is projected onto a second projection plane perpendicular to the direction of the longitudinal axis of the distal end portion 7.

Further, it is preferable that the second direction includes a component in a direction opposite to the direction toward the rotating shaft-connection portion 82A from the arm connection portion 85 in the first projection plane PP1 parallel to the second plane P2 as in this embodiment.

In this case, the second direction may include a component in a direction toward the distal end side of the distal end portion 7 from the arm connection portion 85 as in this embodiment in a state in which the first direction is a direction perpendicular to the first plane P1 in the first projection plane PP1 parallel to the second plane P2.

Figure 20:
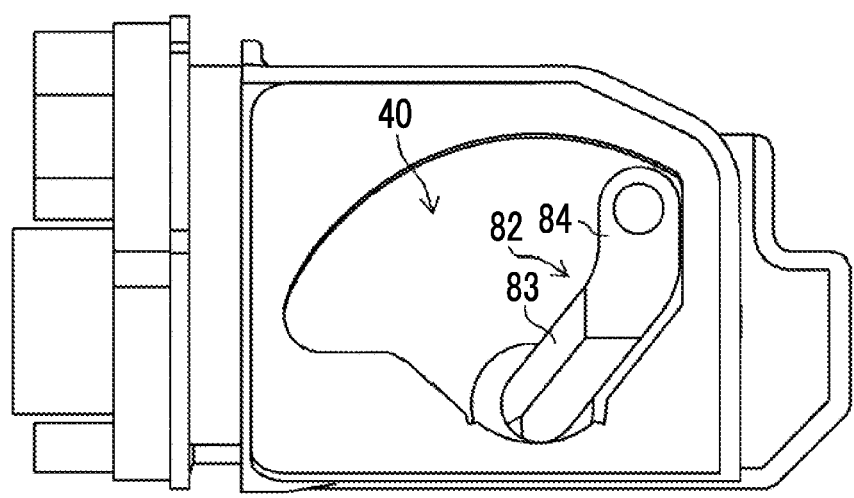
FIG. 20 is a side view showing a standing lever and a standing lever-receiving chamber of another embodiment.

Furthermore, unlike in this embodiment, the second direction may include a component in a direction toward the proximal end side of the distal end portion 7 from the arm connection portion 85 in a state in which the first direction is a direction perpendicular to the first plane P1 in the first projection plane PP1 parallel to the second plane P2. That is, the shape of the standing lever 82 of the drive member 80 and the shape of the standing lever-receiving chamber 40 of this embodiment shown in FIG. 14 may also be horizontally inverted as shown in FIG. 20. In this case, this structure is useful in a case in which a useless space is formed in a region that is close to the distal end of the observation window 22 and the illumination window 24 and is closer to the proximal end than the distal end of the standing lever-receiving chamber 40. That is, since the rotation axis 81A is disposed close to the distal end in the range of the standing lever-receiving chamber 40 in the front-rear direction, the useless space can be reduced. Accordingly, the length of the distal end portion 7 in the front-rear direction (the direction of the longitudinal axis of the distal end portion 7) can be shortened.

Further, in this embodiment, the distal end-side end surfaces 48A and 49A and the proximal end-side end surfaces 48B and 49B of the standing lever-receiving chamber 40 are provided as a rotation restricting portion that restricts the range of rotation of the first arm portion 83 (standing lever 82) about the rotation axis 81A. In a case in which these end surfaces are positioned at the middle position of the range of rotation of the first arm portion 83, the first direction is a direction perpendicular to the first plane P1 (that is, the vertical direction) in the first projection plane PP1 parallel to the second plane P2. However, the first direction does not necessarily need to be limited thereto.

Furthermore, the range of rotation, that is, the rotatable angle of the first arm portion 83 (standing lever 82) is about 90° in this embodiment, but is not limited thereto.

Moreover, the first arm portion 83 of the standing lever 82 of this embodiment is provided along the first direction and the second arm portion 84 is provided along the second direction, but this does not mean that the first and second arm portions 83 and 84 are formed in the shape of a straight line. As long as a straight line, which connects both ends of the first arm portion 83, is along the first direction, the first arm portion 83 may be curved and may be bent at a plurality of positions. The same applies to the second arm portion 84.

EXPLANATION OF REFERENCES

1: endoscope
2: insertion part
3: operation unit
4: universal cord
5: soft portion
6: bendable portion
7: distal end portion
12: standing operation lever
13: treatment tool inlet
20: flat surface
22: observation window
24: illumination window
26: cap
30: distal-end-portion body
32: proximal end portion
34: side wall portion
35: notch portion
36: side wall portion
38: standing base-receiving slit
38a: treatment tool outlet
40: standing lever-receiving chamber
43: protective plate
44: wire insertion hole
46: posterior wall portion
48: first arm receiving portion
48A, 49A: distal end-side end surface
48B, 49A: proximal end-side end surface
48C: inclined surface
48D: tapered surface
48E, 49D, 49E: vertical surface
49: second arm receiving portion
58: holding hole
60: standing base
80: drive member
81: rotating shaft
81A: rotation axis
82: standing lever
82A: rotating shaft-connection portion
82B: wire-connection portion
83: first arm portion
83A: first axis
84: second arm portion
84A: second axis
85: arm connection portion
86: operation wire
88: connector
90: engagement protrusion
P1: first plane
P2: second plane
P3: third plane
PP1: first projection plane

What is claimed is:
1. An endoscope comprising:
an insertion part that includes a distal end, a proximal end, and a longitudinal axis;
a distal-end-portion body that is provided on a distal end side of the insertion part;

an operation unit that is provided on a proximal end side of the insertion part;

a treatment tool-standing base that is provided in the distal-end-portion body;

a standing lever that is provided in the distal-end-portion body, includes a rotating shaft, and allows the treatment tool-standing base to stand and fall; and a transmission member that is provided up to the distal-end-portion body from the operation unit via the insertion part and transmits displacement generated by the operation unit to the standing lever, wherein the standing lever includes a first arm portion that includes a rotating shaft-connection portion to which the rotating shaft is connected, a second arm portion that includes a transmission member-connection portion to which the transmission member is connected, and an arm connection portion that is provided between the first and second arm portions, and in a case in which a plane, which includes an axis of the rotating shaft and is parallel to the longitudinal axis, is referred to as a first plane, a plane, which is perpendicular to the axis of the rotating shaft and crosses the rotating shaft-connection portion, is referred to as a second plane, a direction, which obliquely crosses the second plane, is referred to as a first direction, and a direction, which includes a component in a direction parallel to the second plane and obliquely crosses the first direction in a case in which the direction and the first direction are projected onto a first projection plane parallel to the second plane, is referred to as a second direction, the second arm portion and the arm connection portion are disposed on a side opposite to one side of the second plane on which the treatment tool-standing base is provided, the first arm portion is provided along a first axis and extends from the rotating shaft-connection portion to the arm connection portion, the second arm portion is provided along a second axis and extends from the arm connection portion to the transmission member-connection portion, wherein the first axis extends in the first direction and the second axis extends in the second direction, wherein the second axis is perpendicular to the longitudinal axis of the insertion part when the standing lever is rotated to a first position close to the proximal end side of the insertion part, and the second axis is parallel to the longitudinal axis of the insertion part when the standing lever is rotated to a second position closes to the distal end side of the insertion part.

2. The endoscope according to claim 1, wherein the second direction is a direction parallel to the second plane.

3. The endoscope according to claim 1, wherein the distal-end-portion body includes a rotation restricting portion that restricts the range of rotation of the first arm portion about the axis of the rotating shaft, and the first direction is a direction perpendicular to the first plane in the first projection plane in a case in which the first arm portion is positioned at a middle position of the range of rotation.

4. A treatment tool-standing mechanism of an endoscope including an insertion part that includes a distal end, a proximal end, and a longitudinal axis, a distal-end-portion body that is provided on a distal end side of the insertion part, an operation unit that is provided on a proximal end side of the insertion part, and a treatment tool-standing base that is provided in the distal-end-portion body, the treatment tool-standing mechanism comprising:

a standing lever that is provided in the distal-end-portion body, includes a rotating shaft, and allows the treatment tool-standing base to stand and fall; and a transmission member that is provided up to the distal-end-portion body from the operation unit via the insertion part and transmits displacement generated by the operation unit to the standing lever, wherein the standing lever includes a first arm portion that includes a rotating shaft-connection portion to which the rotating shaft is connected, a second arm portion that includes a transmission member-connection portion to which the transmission member is connected, and an arm connection portion that is provided between the first and second arm portions, and in a case in which a plane, which includes an axis of the rotating shaft and is parallel to the longitudinal axis, is referred to as a first plane, a plane, which is perpendicular to the axis of the rotating shaft and crosses the rotating shaft-connection portion, is referred to as a second plane, a direction, which obliquely crosses the second plane, is referred to as a first direction, and a direction, which includes a component in a direction parallel to the second plane and obliquely crosses the first direction in a case in which the direction and the first direction are projected onto a first projection plane parallel to the second plane, is referred to as a second direction, the second arm portion and the arm connection portion are disposed on a side opposite to one side of the second plane on which the treatment tool-standing base is provided, the first arm portion is provided along a first axis and extends from the rotating shaft-connection portion to the arm connection portion, the second arm portion is provided along a second axis and extends from the arm connection portion to the transmission member-connection portion, wherein the first axis extends in the first direction and the second axis extends in the second direction, wherein the second axis is perpendicular to the longitudinal axis of the insertion part when the standing lever is rotated to a first position close to the proximal end side of the insertion part, and the second axis is parallel to the longitudinal axis of the insertion part when the standing lever is rotated to a second position closes to the distal end side of the insertion part.

* * * * *